United States Patent
Shigetoh et al.

(10) Patent No.: US 7,109,309 B2
(45) Date of Patent: Sep. 19, 2006

(54) PEPTIDE FRUCTOSE AND PROTEIN CONJUGATE WITH THE SAME

(75) Inventors: Nobuyuki Shigetoh, Kyotanabe (JP); Hiroshi Nakayama, Hirakata (JP); Keiko Yugawa, Nara (JP); Fumihisa Kitawaki, Kadoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 442 days.

(21) Appl. No.: 10/312,828

(22) PCT Filed: Jul. 13, 2001

(86) PCT No.: PCT/JP01/06110

§ 371 (c)(1),
(2), (4) Date: Apr. 8, 2003

(87) PCT Pub. No.: WO02/06310

PCT Pub. Date: Jan. 24, 2002

(65) Prior Publication Data

US 2003/0175996 A1    Sep. 18, 2003

(30) Foreign Application Priority Data

Jul. 14, 2000  (JP) ............................. 2000-214053
Nov. 17, 2000  (JP) ............................. 2000-350979

(51) Int. Cl.
C07K 17/10  (2006.01)
C07K 16/18  (2006.01)
C12P 21/08  (2006.01)
G01N 33/531  (2006.01)

(52) U.S. Cl. .................. 530/403; 530/387.9; 530/809; 530/406; 435/70.21; 435/70.2; 436/548; 436/823

(58) Field of Classification Search ............... 436/961, 436/544, 548, 823; 536/1.1; 530/362, 386, 530/403, 391.1, 388.9, 387.1, 387.9, 809; 424/175.1; 435/70.21, 548
See application file for complete search history.

(56) References Cited

U.S. PATENT DOCUMENTS 4,647,654 A * 3/1987 Knowles et al. ............ 530/326

5,632,993 A * 5/1997 Klein et al. ............... 424/194.1
5,718,900 A * 2/1998 Hill et al. ................ 424/194.1

FOREIGN PATENT DOCUMENTS

| EP | 0 185 870 A2 | 10/1985 |
| EP | 0 201 187 A1 | 3/1986 |
| EP | 0 547 029 A1 | 2/1989 |
| JP | 4-89487 | 3/1992 |
| JP | 06/225790 | 8/1994 |
| JP | 07051087 | 2/1995 |
| JP | 08092300 | 4/1996 |
| WO | WO 91/02978 | 3/1991 |

OTHER PUBLICATIONS

T. Azuma, et al., "Maturation of the Immune Response to (4-Hydroxy-3-Nitrophenyl)-Acetyl (NP) Haptens In C57BL/8 Mice", Molecular Immunology. 24(3) 287-296 (1987).

* cited by examiner

Primary Examiner—Mary E. Ceperley
Assistant Examiner—Shafiqul Haq
(74) Attorney, Agent, or Firm—Snell & Wilmer LLP (57) ABSTRACT

It is intended to provide an antibody specific to HbA1c, antibody-producing cells capable of supplying the antibody in a stable state in the future, and a method of constructing the antibody-producing cells without any probability factors, and a method which comprises fusing mouse spleen cells, which have been sensitized with an immunogen composed of a compound containing the following structural formula (I) and a binding protein, with a myeloma-origin cell line, obtaining monoclonal antibody-producing cells by cloning, and then purifying and acquiring the monoclonal antibody produced by these cells into the culture supernatant

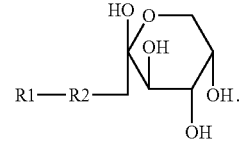

(I)

11 Claims, 6 Drawing Sheets

PEPTIDE FRUCTOSE AND PROTEIN CONJUGATE WITH THE SAME

RELATED APPLICATIONS

This is a US national phase filing under 35 U.S.C. § 371 of PCT/JP1/06110 filed Jul. 13, 2001 and claims priority from JP 2000-214053 filed Jul. 14, 2000 and JP 2000-350979 filed Nov. 17, 2000.

TECHNICAL FIELD

The present invention relates to a peptide fructose compound, which can be used as an immunogen for production of antibodies for hemoglobin A1c (hereinafter abbreviated as HbA1c). The present invention also relates to a protein conjugate of the compound and a protein, and an antiserum and an antibody obtained using the peptide fructose-protein conjugate.

BACKGROUND ART

Conventionally, as an immunogen required for production of anti-HbA1c antibodies, HbA1c itself has been generally used. HbA1c has a structure similar to that of hemoglobin A0 (hereinafter abbreviated as HbA0) which constitutes 90% of the total amount of hemoglobin. Whereas HbA0 has no sugar chain at the N-terminus of its β chain, HbA1c has a fructose binding to the N-terminus of its β chain. This is the only difference between HbA0 and HbA1c. Therefore, most of the antibodies which are produced using HbA1c itself as an immunogen can also recognize HbA0. Among the antibodies for hemoglobin, there are only a small number of antibodies capable of recognizing only HbA1c. Conventionally, such a group of antibodies have been screened for those that bind to HbA1c.

Such screening work is labor-intensive and costly. Therefore, it may be conceived to use an epitope capable of recognizing only HbA1c. However, in most cases, an epitope alone does not have sufficient antigenicity or immunogenicity in production of an antiserum or antibodies. Therefore, an animal is immunized with an epitope in conjunction with an adjuvant or a carrier. However, immunization of an animal with a carrier and an epitope is conventionally labor-intensive and is not necessarily efficient to obtain an intended antiserum or antibodies, and is also costly. Moreover, acquisition of an intended antibody depends on probabilistic factors, and the above-described method cannot be said to be reliable. No monoclonal antibody without cross reactivity to HbA0 has been obtained, and there has been conventionally no established method with which such a monoclonal antibody can be reliably and simply produced.

In order to solve the above-described problems, an object of the present invention is to provide a peptide fructose compound and a protein conjugate which are immunogens capable of producing anti-HbA1c antibodies, preferably only anti-HbA1c antibodies, where the probabilistic factors are removed and the antibodies have no cross reactivity to HbA0. Another object of the present invention is to provide an antiserum or antibodies produced using such a peptide fructose compound or a protein conjugate. Still another object of the present invention is to provide a method of producing an antibody-producing cell capable of supplying an antibody specific to HbA1c and without cross reactivity to HbA0 and capable of stably supplying such an antibody for future use, where the probabilistic factors are removed.

DISCLOSURE OF THE INVENTION

In order to achieve the above-described objects, the present invention provides the following.

In one aspect, the present invention provides a peptide fructose compound represented by formula (I) below:

(I)

wherein R1 represents any molecule having an —SH group, the R1 is linked to the carboxy-terminus of R2 at (b) with a covalent bond, the R2 contains one or more amino acids derived from the amino acid sequence of HbA1 or an amino acid analog functionally equivalent to the amino acids, and the R2 is linked to the fructose at the amino-terminus thereof.

Here, the molecule having an —SH may be any molecule known in the art. Examples of such a molecule include, but are not limited to, cysteine and homocysteine. The linkage (b) is usually made by a covalent bond, and may be made by any type of bond (e.g., a hydrogen bond) other than a covalent bond as long as the bond has an ability to induce an antibody or an antiserum. The covalent bond may be any type of covalent bond, and preferably a peptide bond (amide bond). Moreover, instead of the above-described fructose, any molecule (e.g., other sugars) functionally equivalent thereto may be used.

In another embodiment, the R2 may contain at least a peptide represented by formula (II) below:

(II)

In one embodiment, the R2 may contain at least a peptide represented by formula (III) below:

(III)

In another embodiment, the R1 may contain at least one cysteine residue. In another embodiment, the R1 may comprise a peptide or a peptide analog. In another embodiment, the R1 may comprise a peptide. In another embodiment, the R1 may be a cysteine residue.

In another embodiment, the covalent bond at (b) is a peptide bond.

In another aspect, the present invention provides a protein conjugate, wherein a peptide fructose compound according to any one of claims 1 to 8 is linked with a protein. Preferably, this protein may not be hemoglobin, or may be hemoglobin which has no cross reactivity to hemoglobin A1c.

In one embodiment, the protein is selected from the group consisting of bovine serum albumin (BSA), chicken-γ globulin (CGG), and Keyhole Limpet Hemocyanin (KLH). Preferably, the protein is CGG.

In another aspect, the present invention provides an antiserum, produced in the blood of an animal by injecting a peptide fructose compound of the present invention or a protein conjugate of the present invention.

In another aspect, the present invention provides an antibody, isolated from an antiserum of the present invention.

In another aspect, the present invention provides a monoclonal antibody-producing cell, wherein the monoclonal antibody-producing cell is obtained by fusing a spleen cell of a mouse sensitized with a peptide fructose compound of the present invention or a protein conjugate of the present invention, with a myeloma-derived cell, and cloning a fused cell, and the monoclonal antibody-producing cell produces a monoclonal antibody capable of specifically binding to human hemoglobin A1c. In one embodiment, the present invention provides a monoclonal antibody-producing cell designated as deposit number FERM BP-7637 or FERM BP-7636.

In another aspect, the present invention provides a method of producing a monoclonal antibody-producing cell capable of producing a monoclonal antibody capable of specifically binding to human hemoglobin A1c. The method comprises the steps of:

a) sensitizing a mouse with a peptide fructose of the present invention or a protein conjugate of the present invention; and b) isolating a spleen cell from the sensitized mouse, and fusing the spleen cell with a myeloma-derived cell.

In another aspect, the present invention provides a monoclonal antibody, produced by a monoclonal antibody-producing cell of the present invention, which specifically binds to human hemoglobin A1c.

In one embodiment, the binding constant to human hemoglobin A1c thereof may be $10^4$ or more. Preferably, the binding constant may be $10^5$ or more, $10^6$ or more, $10^7$ or more, $10^8$ or more, $10^9$ or more, or $10^{10}$ or more.

BEST MODE FOR CARRYING OUT THE INVENTION

Hereinafter, some terms used herein will be described. It should be noted that unless otherwise defined, all technical and scientific terms used herein have the same meaning as commonly understood by one of ordinary skill in the art to which this invention belongs.

The term "peptide fructose compound" refers to a compound comprising a peptide and fructose. A typically peptide fructose compound has the following structure:

(I)

where R1 represents any molecule having an —SH group; the R1 is linked to the carboxy terminus of R2 by covalent bond at (b); and R2 includes one or more amino acids derived from HbA1 or amino acid analogs functionally equivalent to the amino acids, and the R2 is linked to fructose at the amino-terminus thereof.

The term "peptide", "oligopeptide", "polypeptide" and "protein" are used interchangeably to refer to a polymer of two or more amino acids (naturally occurring or non-naturally occurring) with peptide bonds.

The term "amino acid" refers to an organic compound having an amino group (—NH$_2$) and a carboxy group (—COOH) in the same molecule, and as used in the art, also includes imino acids having an imino group, such as proline and hydroxyproline. Amino acids used herein may be naturally-occurring amino acids (asparagine (hereinafter abbreviated as Asn), aspartic acid (hereinafter abbreviated as Asp), alanine (hereinafter abbreviated as Ala), arginine (hereinafter abbreviated as Arg), isoleucine (hereinafter abbreviated as Ile), glycine (hereinafter abbreviated as Gly), glutamine (hereinafter abbreviated as Gln), glutamic acid (hereinafter abbreviated as Glu), cysteine (hereinafter abbreviated as Cys), serine (hereinafter abbreviated as Ser), tyrosine (hereinafter abbreviated as Tyr), tryptophan (hereinafter abbreviated as Trp), threonine (hereinafter abbreviated as Thr), valine (hereinafter abbreviated as Val), histidine (hereinafter abbreviated as His), phenylalanine (hereinafter abbreviated as Phe), proline (hereinafter abbreviated as Pro), methionine (hereinafter abbreviated as Met), lysine (hereinafter abbreviated as Lys), and leucine (hereinafter abbreviated as Leu)), or non-naturally occurring amino acids. The amino acid may be an α-amino acid, β-amino acid, γ-amino acid, δ-amino acid, ω-amino acid, or the like. The amino acid may be of the L type or D type, and is preferably of the L type.

The term "non-naturally occurring amino acid" refers to an amino acid which is not found in a naturally-occurring protein. Examples of the non-naturally occurring amino acid include norleucine, para-nitrophenylalanine, homophenylalanine, para-fluorophenylalanine, 3-amino-2-benzylpropionic acid, D- or L-homoarginine, and D-phenylalanine. The non-naturally occurring amino acid also includes ones with an —SH group, such as homocysteine.

The term "amino acid analog" refers to a molecule having a physical property or a function similar to that of an amino acid, but is not an amino acid itself. Examples of amino acid analogs include ethionine, canavanine, and 2-methylglutamine. The similarity of such a physical property or function of an amino acid analog may be determined based on whether or not the linkage of the analog to other compounds is substantially the same as that of the amino acid, as described herein.

For a peptide fructose compound of the present invention, amino acid substitution and the like, with substantially no change in functionality, is performed by chemical synthesis or by changing a codon coding an amino acid in a DNA sequence using genetic engineering techniques. The present invention is not so limited.

A certain amino acid may be substituted with another amino acid in a protein structure, for example, a cationic region or a binding site for a substrate molecule, without significant reduction or loss of interactive binding capability. The biological function of a certain protein is determined by the interaction capability and properties of the protein. Therefore, even if substitution of a particular amino acid is performed in an amino acid sequence (or at the DNA code sequence level), a protein may maintain its original properties after the substitution. Therefore, peptides disclosed herein or DNA encoding the peptides may be modified in various manners without clearly impairing their biological utility.

When the above-described modifications are designed, the hydrophobicity index of amino acids may be taken into consideration. The hydrophobic amino acid index plays an important role in providing a protein with an interactive biological function, which is generally recognized in the art (Kyte. J and Doolittle, R. F., J. Mol. Biol. 157(1):105–132, 1982). The hydrophobic property of an amino acid contributes to the secondary structure of a generated protein and then regulates interactions between the protein and other molecules (e.g., enzymes, substrates, receptors, DNA, antibodies, antigens, etc.). Each amino acid is given a hydrophobicity index based on the hydrophobicity and charge properties thereof as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5)).

It is well known that if a certain amino acid is substituted with another amino acid having a similar hydrophobicity index, a resultant protein may still have a biological function similar to that of the original protein (e.g., a protein having an equivalent enzymatic activity). For such an amino acid substitution, the hydrophobicity index is preferably within ±2, more preferably within ±1, and even more preferably within ±0.5. It is understood in the art that such an amino acid substitution based on hydrophobicity is efficient. As described in U.S. Pat. No. 4,554,101, amino acid residues are given the following hydrophilicity indexes: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid may be substituted with another amino acid which has a similar hydrophilicity index and can still provide a biological equivalent. For such an amino acid substitution, the hydrophilicity index is preferably within ±2, more preferably within ±1, and even more preferably within ±0.5.

The term "conservative substitution" as used herein refers to amino acid substitution in which a substituted amino acid and a substituting amino acid have similar hydrophilicity indexes or/and hydrophobicity indexes. Examples of conservative substitutions, which are well known to those skilled in the art, include, but are not limited to, substitutions within each of the following groups: arginine and lysine; glutamic acid and aspartic acid; serine and threonine; glutamine and asparagine; and valine, leucine, and isoleucine.

Herein, in order to produce functionally equivalent peptide fructose compounds, amino acid addition, deletion, substitution, or modification can be performed. Amino acid substitution refers to substitution of one or more amino acids in an original peptide, for example, 1 to 10 amino acids, preferably 1 to 5, and more preferably 1 to 3. Amino acid addition refers to addition of one or more amino acids to an original peptide chain, for example, 1 to 10 amino acids, preferably 1 to 5, and more preferably 1 to 3. Amino acid deletion refers to deletion of one or more amino acids from an original peptide, for example, 1 to 10 amino acids, preferably 1 to 5, and more preferably 1 to 3. Amino acid modification includes, but is not limited to, amidation, carboxylation, sulfation, halogenation, alkylation, glycosylation, phosphorylation, hydration, acylation (e.g., acetylation), and the like. An amino acid for substitution or addition may be a naturally-occurring amino acid or alternatively a non-naturally-occurring amino acid. A naturally-occurring amino acid is preferable.

The term "peptide analog" refers to a compound equivalent to a peptide with respect to at least one chemical or biological function, but not a peptide itself. Therefore, a peptide analog includes a peptide in which one or more amino acid analogs have been added to the original peptide or one or more amino acids have been substituted with an amino acid analog. A peptide analog has such additions or substitutions in which a function of the peptide is substantially the same as that of the original peptide (e.g., a similarity of pKa values, a similarity of functional groups, a similarity of linkage with other molecules, a similarity of water solubility, and the like). Such a peptide analog can be produced using techniques well known in the art.

In one aspect, a peptide fructose of the present invention is a peptide fructose compound represented by the following formula (I).

(I)

A peptide fructose compound typically comprises an introduced moiety having an —SH group (e.g., a cysteine residue) in addition to fructose-valine-histidine which is a characteristic structure of HbA1c, which makes it easy to bind to a protein. Therefore, a protein conjugate can be produced by binding a peptide fructose compound to a protein.

A protein conjugate of the present invention is characterized in that a peptide fructose compound represented by formula (I) is linked with a protein excluding hemoglobin. The protein conjugate typically has fructose-valine-histidine, which is a characteristic structure of HbA1c, and a protein excluding hemoglobin, and thus, does not have a structure common to hemoglobin HbA0. Therefore, the protein conjugate can be used as an immunogen to reliably produce an anti-HbA1c antibody without cross reactivity to hemoglobin HbA0, and preferably without cross reactivity to hemoglobins other than HbA1c.

In a peptide fructose-protein conjugate, a peptide fructose compound represented by formula (I) is linked to a protein, excluding hemoglobin, via an —SH group, preferably via a disulfide bond. The peptide fructose compound can be easily linked to a protein via a thiol group (functional group) such as cysteine to easily produce a protein conjugate. Moreover, the amount of the peptide fructose compound reacting with a protein can be controlled and the amount of the peptide fructose compound introduced into a protein can be measured. Another advantage of the introduction of an —SH group is formation of a relatively stable disulfide (S—S) bond, for example.

As the protein, any protein other than hemoglobin can be used without particular limitation. Examples of the protein include bovine serum albumin (hereinafter abbreviated as BSA), chicken-γ globulin (hereinafter abbreviated as CGG), and Keyhole Limpet hemocyanin (hereinafter abbreviated as KLH).

In formula (I), R2 preferably includes a residue represented by the following formulas (II) or (III).

The peptide fructose compound has an introduced structure, leucine-threonine, which is a characteristic structure of HbA1c, in addition to fructose-valine-histidine. This peptide fructose compound can be used to produce an anti-HbA1c antibody which has a higher level of ability to bind to HbA1c and/or a high level of selectivity to HbA1c.

In formula (I), when R2 contains a number of amino acids, which constitute a characteristic structure of HbA1c, or multimers of the amino acids, an anti-HbA1c antibody having a greater binding strength to HbA1c can be preferably produced. Note that when the number of the amino acid multimers which are the characteristic structure of HbA1c is excessively large, the cross reactivity of the obtained anti-HbA1c antibody to hemoglobins other than HbA1c is likely to be high. Therefore, the number of amino acid multimers which are the characteristic structure of HbA1c in R1 and R2 is adjusted from a viewpoint of the binding strength, and the cross reactivity to hemoglobins other than HbA1c, of the obtained anti-HbA1c antibody.

Here, a protein, such as CGG, is preferably used as a protein for producing a protein conjugate of the present invention. CGG is a protein which has no similarity to murine protein and a high level of capability to induce immunity. CGG also has a high level of solubility, which is another reason that CGG is appropriate for use in the present invention. A peptide fructose compound of the present invention can be introduced into such a protein at a rate of at least 10 peptide fructose compounds per protein, preferably at least 20 peptide fructose compounds per protein, more preferably at least 25 peptide fructose compounds per protein, and even more preferably at least 30 per protein. By introducing a number of peptide fructose compounds of the present invention per protein in this manner, it is possible to produce antiserum or antibodies more efficiently.

As a reagent used for linking a peptide fructose compound with a protein, any compound having a functional group capable of reacting with a thiol group of a residue, such as cysteine having a thiol group, and a functional group capable of reacting with an amino group or carboxy group in the protein, can be used. Examples of such a compound include N-γ-maleimidebutyryloxy-succinimide ester (hereinafter abbreviated as GMBS), succinimidyl 4-(N-maleimidemethyl)cyclohexane-1-carboxylate (hereinafter abbreviated as SMCC), succinimidyl 4-(p-maleimidephenyl)butylate (hereinafter abbreviated as SMPB), 4-succinimidyloxycarbonylmethyl-α-(2-pyridyldithio)tolu ene (hereinafter abbreviated as SMPT), and O-succinimidyl-3-(2-pyridyldithio)-1-propionate (hereinafter abbreviated as SPDP). Among them, one which is easily available and can be used to measure the number of peptide fructoses introduced into a protein, is preferable. Such a reagent is SPDP, for example.

An antiserum of the present invention is characterized in that the antiserum is produced in the blood of an animal into which the above-described peptide fructose-protein conjugate has been administered. The antiserum has less cross reactivity to hemoglobins other than HbA1c and can recognize the characteristic structure of HbA1c.

As an animal for producing an antiserum, any conventional animal for immunization can be used without particular limitation. Example of such an animal include mice, rats, rabbits, goats, sheep, and horses. Also, by producing hybridomas using spleen cells from a mouse immunized with a peptide fructose-protein conjugate of the present invention, an anti-HbA1c monoclonal antibody can be produced. An antibody of the present invention may be humanized. A method of humanizing an antibody is well known in the art.

In order to achieve the above-described objects, a monoclonal antibody of the present invention is produced by fusing a spleen cell, which is derived from a mouse sensitized with an immunogen comprising a conjugate of a peptide fructose compound having a structure represented by formula (I) and a protein, with a cell line derived from myeloma, followed by cloning, and allowing a monoclonal antibody-producing cell obtained by cloning to produce the monoclonal antibody in a supernatant of culture medium.

A monoclonal antibody-producing cell of the present invention may be obtained by fusing a spleen cell, which is derived from a mouse sensitized with an immunogen comprising a peptide fructose and a protein, with a myeloma-derived cell line, followed by cloning.

A monoclonal antibody of the present invention is produced by a fusion cell (hybridoma) of a spleen cell, which is derived from a mouse immunized with a peptide fructose compound of the present invention or a protein conjugate therewith as an immunogen, with a myeloma-derived cell. However, a supernatant from a culture in which fusion cells (hybridomas) have been grown can be purified using an antibody purification column filled with protein A Sepharose gel or the like to obtain an antibody of interest.

A peptide fructose compound of the present invention has fructose-valine-histidine which is a characteristic structure of HbA1c. The peptide fructose compound linked with a protein is an effective immunogen for obtaining an anti-HbA1c antibody.

A monoclonal antibody-producing cell of the present invention can be obtained as follows: a spleen cell, which is derived from a mouse immunized as described above, is fused with, for example, a myeloma-derived cell, such as p3×63·Ag8·653 using a fusion accelerating reagent, such as polyethylene glycol, and a number of the resultant fusion cells are screened for one which produces only an antibody which reacts with HbA1c but not HbA0, using an assessment method, such as an enzyme-linked immunosolvent assay (hereinafter abbreviated as ELISA).

EXAMPLES

Hereinafter, the present invention will be described in more detail by way of examples. It should be understood that examples provided below indicate illustrative embodiments of the present invention, and are not intended to limit the present invention. Note that in the examples, CGG was used as an exemplary protein.

Example 1

Preparation of Peptide Fructose

In Example 1, a peptide fructose represented by formula (V) below was prepared by the following procedure.

(V)

1. Introduction of Cys Group Into Wang Resin (Solid Phase)

12.95 g (30 mmol) of N-fluorenylmethoxycarbonyl-S-t-butylthiocysteine (hereinafter abbreviated as Fmoc-Cys (StBu)) was dissolved in 50 ml of chloroform, followed by addition of 3.095 g (15 mmol) of dicyclohexylcarbodiimide (hereinafter abbreviated as DCC) and stirring at room temperature for 10 minutes. The resultant precipitate (dicyclohexyl urea) was filtered out and a filtrate was dried under reduced pressure. The dried filtrate was dissolved in 50 ml of dimethylformamide (hereinafter abbreviated as DMF), followed by addition of 10 g of Wang resin (binding OH group: 1 mmol/g) to obtain a suspension. 0.733 g (6 mmol) of dimethylaminopyridine (hereinafter abbreviated as DMAP) was added to the suspension, and stirred at room temperature for 60 minutes. The reaction solution was subjected to filtration and the resin was washed with DMF twice and then chloroform twice, followed by drying under vacuum overnight to obtain 11.8 g of dried resin (hereinafter abbreviated Fmoc-Cys(StBu)-Resin).

Thereafter, the degree of introduction of a Cys group into the resin was measured by the following manner. 5 ml of 50% piperidine/DMF mixed solution was added to 100 mg of the dried resin, and stirred at room temperature for 5 minutes. The resin was filtered out and the absorbance resultant filtrate was measured at 301 nm. The absorbance was 66.4. The absorption at 301 nm was derived from fluorenylmethylpiperidine (hereinafter abbreviated as Fmp) generated by piperidine deprotecting the Fmoc-Cys group introduced into the resin. Therefore, the amount of released Fmp indicates the amount of a Cys group. The Fmp concentration [Fmp] can be calculated by formula (1), where the molar absorbance coefficient of Fmp at 301 nm is 7800.

$$[\text{Fmp}] = 66.4/7800 \quad \text{(Formula 1)}$$
$$= 8.513 \times 10^{-3} \text{ (M)}$$

Since the reactive OH group of the resin is 1 mmol/g, the concentration of the reactive OH group is roughly calculated to be 0.02 M. Therefore, the rate of introduction of the Cys group into the resin can be calculated by formula (2).

$$(\text{Ratio of introduction of Cys groups}) = 8.513 \times 10^{-3}/0.02 \quad \text{(Formula 2)}$$
$$= 0.43\,(43\%)$$

2. Introduction of His Group Into Fmoc-Cys(StBu)-Resin 10 g (4.3 mmol on a Cys basis) Fmoc-Cys(StBu)-Resin was dispersed in 50 ml of 20% piperidine/DMF, and stirred at room temperature for 10 minutes. The solvent was removed by filtration and thereafter 20% piperidine/DMF reaction was repeated. The resin was washed with 50 ml of DMF three times, and a small amount of the resin was subjected to a ninhydrin test in a methanol solution. As a result, it was confirmed that the amino group was in a free state. The resin was dispersed in 20 ml of DMF. To this solution, 8.447 g (10.75 mmol) of fluorenylmethoxycarbonyltritylhistidine pentafluorophenylester (hereinafter abbreviated as Fmoc-His(Trt)-Opfp) was added, and stirred at room temperature for two hours. The resin was washed with 50 ml of DMF three times. Thereafter, a small amount of resin was subjected to a ninhydrin test in a methanol solution. As a result, it was confirmed that no free amino group existed. Thereafter, the resin was washed with chloroform three times, followed by drying under vacuum overnight to obtain 11.2 g of the dried resin (hereinafter abbreviated as Fmoc-His(Trt)-Cys(StBu)-Resin).

The ratio of introduction of a His group into the resin was measured in a manner as described above. The ratio of introduction of a His group was 38%.

3. Introduction of Valine Group (Hereinafter Abbreviated as Val) Into Fmoc-His(Trt)-Cys(StBu)-Resin 11 g (4.2 mmol on a His basis) Fmoc-His(Trt)-Cys(StBu)-Resin was dispersed in 100 ml of 20% piperidine/DMF, and stirred at room temperature for 10 minutes. The solvent was removed by filtration and thereafter 20% piperidine/DMF reaction was repeated. The resin was washed with 50 ml of DMF three times, and a small amount of the resin was subjected to a ninhydrin test in a methanol solution. As a result, it was confirmed that the amino group was in a free state. The resin was dispersed in 20 ml of DMF. To this solution, 5.234 g (10.53 mmol) of fluorenylmethoxycarbonyltritylvaline pentafluorophenylester (hereinafter abbreviated as Fmoc-Val-Opfp) was added, and stirred at room temperature for two hours. The resin was washed with 50 ml of DMF three times. Thereafter, a small amount of resin was subjected to a ninhydrin test in a methanol solution. As a result, it was confirmed that no free amino group existed. Thereafter, the resin was washed with chloroform three times, followed by drying under vacuum overnight to obtain 10.0 g of the dried resin (hereinafter abbreviated as Fmoc-Val-His(Trt)-Cys(StBu)-Resin).

The ratio of introduction of a Val group into the resin was measured in a manner as described above. The ratio of introduction of a Val group was 21%.

4. Removal of Peptide Chain From Resin 9 g of Fmoc-Val-His(Trt)-Cys(StBu)-Resin was dispersed in 100 ml of 20% piperidine/DMF, and stirred at room temperature for 10 minutes. The solvent was removed by filtration. Thereafter, the resin was reacted with 20% piperidine/DMF again. The resin was washed with 100 ml of DMF three times. A small amount of the resin was subjected to a ninhydrin test in a methanol solution. As a result, it was confirmed that the amino acid group was in a free state. The resin was washed with chloroform three times, and thereafter, was dispersed in 100 ml of 50% chloroform/trifluoroacetic acid (hereinafter abbreviated as TFA) mixed solvent, and stirred at room temperature for two hours. The resin was filtered out, and washed with 100 ml of chloroform/TFA (=4/1) mixed solvent two times. All of the filtrate and the washing solution were collected and concentrated under reduced pressure. The residue was dissolved in a small amount of TFA, and dispersed in about 300 ml of ether, followed by centrifugation. The supernatant was removed and the precipitate was washed with ether two times, followed by drying under vacuum overnight. As a result, 0.63 g of the crude product (Val-His-Cys) was obtained.

5. Introduction of Fructose Into Peptide Chain Due to Amadori Rearrangement Reaction 500 mg (1.126 mmol) of synthetic peptide (Val-His-Cys) and 270 mg (1.5 mmol) of glucose were dissolved in 25 ml of pyridine/acetic acid (=1/1) mixed solvent, and stirred in a dark place at room temperature for 5 days. The solvent was removed under vacuum, and thereafter, the residue was dissolved in 25 ml of water, followed by concentration under vacuum. The concentrate was dissolved in a small amount of water and loaded onto a Dowex50WX8 column (manufactured by Sigma, diameter 3.5 cm×length 25 cm) which was a strongly acidic ion exchange resin. The column was washed with about 2 L of water to remove the glucose. Thereafter, the product was eluted with, 1 N ammonia water, and the eluate was lyophilized. The resultant product was dissolved in 0.1 M triethylammonium buffer (pH=8.2), and loaded onto an Affigel 601 column (manufactured by Pharmacia, diameter 1.7 cm×length 20 cm). The column was washed with 1 L of 0.1 M triethylammonium buffer (pH=8.2) and then 1 L of water. Finally, the product was eluted with 0.1% formic acid, and the eluate was lyophilized. 50 mg of a crudely purified product of peptide fructose (fructose-Val-His-Cys) was obtained. Table 1 shows chemical shifts and peak positions of NMR for the product measured in deuterated methanol.

TABLE 1

| Chemical shift (δ, ppm) | Number of hydrogens | Number of peaks | Peak position (numeral in the formula above) |
|---|---|---|---|
| 1.14 | 6 | 4 | 1 |
| 2.20 | 1 | m | 2 |
| 2.93 | 2 | 8 | 9 |
| 3.22 | 2 | 8 | 5 |
| 3.5–3.9 | 7 | m | 10–14 |
| 3.76 | 1 | 2 | 3 |
| 4.60 | 1 | 3 | 8 |
| 4.82 | 1 | 3 | 4 |
| 7.38 | 1 | 1 | 6 |
| 8.77 | 1 | 1 | 7 |

Note:
m indicates a large number of peaks.

(Preparation of Peptide Fructose-Protein Conjugate)

In this example, CGG was used as a protein.

1. Preparation of pyridyldithiopropionylated CGG (CGG-SPDP))

200 mg ($1.33 \times 10^{-3}$ mmol) of CGG was dissolved in 50 ml of phosphate buffer saline (hereinafter abbreviated as PBS). 5 ml of SPDP/ethanol solution (SPDP=40 mg, 0.13 mmol, an equivalent weight of 100) was dropped into the mixture while stirring. After stirring at room temperature for 30 minutes, the resultant precipitate was removed by centrifugation (10 minutes, 20,000 rpm). The resultant supernatant was subjected to gel filtration using a Sephadex G25M column (manufactured by Pharmacia, diameter 2 cm×length 80 cm) to obtain 80 ml of CGG-SPDP/PBS solution.

The number of SPDPs binding to one CGG molecule was determined as follows. 1 ml of the resultant CGG-SPDP PBS solution was used and the absorbance thereof was measured at 280 nm. The absorbance was 3.73.

50 μl of 100 mM dithiothreitol (hereinafter abbreviated as DTT) aqueous solution was added to the CGG-SPDP/PBS solution, and was allowed to stand for 5 minutes. Thereafter, the absorbance was measured at 343 nm, with a result of 2.80.

Assuming that the molecular absorbance coefficient of pyridine-2-thione released by DTT reduction at 343 nm was $8.08 \times 10^3$, the concentration [pyridine-2-thione] was determined by formula (3).

$$[\text{pyridine-2-thione}] = 2.80/(8.08 \times 10^3) \quad \text{(Formula 3)}$$
$$= 3.47 \times 10^{-4} \text{ (M)}$$

This concentration is equivalent to the concentration of SPDP introduced into CGG. Also, since the 2-pyridyldisulfide group of SPDP contributes to the absorbance at 280 nm, calculation of the CGG concentration requires the following correction. The absorbance at 280 nm attributed to CGG (A280, CGG) can be calculated by formula (4) below, where the molecular absorbance coefficient of a 2-pyridyldisulfide group at 280 nm is $5.1 \times 10^3$.

$$(A280, CGG) = 3.73 - (3.4 \times 10^{-4} \times 5.1 \times 10^3) \quad \text{(Formula 4)}$$

$$= 1.96$$

Therefore, the CGG concentration [CGG], and the number of SPDP molecules introduced into one CGG molecule [SPDP]/[CGG] can be calculated by formula (5) below, where the molar absorbance coefficient of CGG at 280 nm is $1.99 \times 10^5$.

$$[CGG] = 1.96/(1.99 \times 10^5) \quad \text{(Formula 5)}$$
$$= 9.85 \times 10^{-6} \text{ (M)}$$
$$[SPDP]/[CGG] = 3.47 \times 10^{-4}/(9.85 \times 10^{-6})$$
$$= 35.2$$

2. Preparation of Conjugate of Peptide Fructose and CGG 40 mg ($7.18 \times 10^{-2}$ mmol) of a pyridyldithio-derivative was added to 50 ml of CGG-SPDP/PBS solution, and stirred at 4° C. overnight. The resultant precipitate was removed by centrifugation (10 minutes, 20,000 rpm), and thereafter, the absorbance (A343) was measured at 343 nm, with a result of 3.52. The resultant supernatant was subjected to gel filtration using a Sephadex G25 column (manufactured by Pharmacia, diameter 2 cm×length 80 cm). As a result, 48 ml of a conjugate of peptide fructose and CGG was obtained.

The number of peptide fructoses binding to one CGG molecule was determined as follows. Assuming that the molecular absorbance coefficient of released pyridine-2-thione at 343 nm is $8.08 \times 10^3$ based on the above-described result that A343 was 3.52 immediately after the reaction, the concentration [pyridine-2-thione] can be calculated by formula (6) below.

$$[\text{pyridine-2-thione}] = 3.52/(8.08 \times 10^3) \quad \text{(Formula 6)}$$

$$= 4.35 \times 10^{-4} \ (M)$$

This concentration is equivalent to the concentration of peptide fructose introduced into CGG. Since the CGG concentration was $1.40 \times 10^{-5}$ M, the number of peptide fructose molecule introduced into one CGG molecule [peptide fructose]/[CGG] can be calculated by formula (7).

$$[\text{peptide fructose}]/[CGG] = 4.35 \times 10^{-4}/(1.40 \times 10^{-5}) \quad \text{(Formula 7)}$$

$$= 31.1$$

Example 2

Preparation of Peptide Fructose

In this example, peptide fructose represented by formula (VI) below was prepared by the following procedure.

1. Introduction of Cys Group Into Wang Resin (Solid Phase)

Fmoc-Cys(StBu)-Resin was prepared in a manner as described in Example 1.

2. Introduction of Thr Group Into Fmoc-Cys(StBu)-Resin 19.2 g (7.668 mmol on a Cys basis) Fmoc-Cys(StBu)-Resin was dispersed in 50 ml of 20% piperidine/DMF, and stirred at room temperature for 10 minutes. The solvent was removed by filtration and thereafter the 20% piperidine/DMF reaction was repeated. The resin was washed with 50 ml of DMF three times, and a small amount of the resin was subjected to a ninhydrin test in a methanol solution. As a result, it was confirmed that the amino group was in a free state. The resin was dispersed in 20 ml of DMF. To this solution, 9.719 g (19.17 mmol) of fluorenylmethoxycarbonylthreonine pentafluorophenylester (hereinafter abbreviated as Fmoc-Thr-Opfp) was added, and stirred at room temperature for two hours. The resin was washed with 50 ml of DMF three times. Thereafter, a small amount of resin was subjected to a ninhydrin test in a methanol solution. As a result, it was confirmed that no free amino group existed. Thereafter, the resin was washed with chloroform three times, followed by drying under vacuum overnight to obtain 17.2 g of the dried resin (hereinafter abbreviated as Fmoc-Thr-Cys(StBu)-Resin).

The ratio of introduction of a Thr group into the resin was measured in a manner as described in Example 1. The ratio of introduction of a Thr group was 42%.

3. Introduction of Leu Group Into Fmoc-Thr-Cys(StBu)-Resin 15.2 g (6.444 mmol on a Cys basis) Fmoc-Thr-Cys (StBu)-Resin was dispersed in 50 ml of 20% piperidine/DMF, and stirred at room temperature for 10 minutes. The solvent was removed by filtration and thereafter 20% piperidine/DMF reaction was repeated. The resin was washed with 50 ml of DMF three times, and a small amount of the resin was subjected to a ninhydrin test in a methanol solution. As a result, it was confirmed that the amino group was in a free state. The resin was dispersed in 20 ml of DMF. To this solution, 8.361 g (16.11 mmol) of fluorenylmethoxycarbonylleucine pentafluorophenylester (hereinafter abbreviated as Fmoc-Leu-Opfp) was added, and stirred at room temperature for two hours. The resin was washed with 50 ml of DMF three times. Thereafter, a small amount of resin was subjected to a ninhydrin test in a methanol solution. As a result, it was confirmed that no free amino group existed. Thereafter, the resin was washed with chloroform three times, followed by drying under vacuum overnight to obtain 13.4 g of the dried resin (hereinafter abbreviated as Fmoc-Leu-Thr-Cys(StBu)-Resin).

The ratio of introduction of a Leu group into the resin was measured in a manner as described above. The ratio of introduction of a Leu group was 26%.

4. Introduction of His Group Into Fmoc-Leu-Thr-Cys(StBu)-Resin

Fmoc-His(Trt)-Leu-Thr-Cys(StBu)-Resin was prepared in a manner as described in Example 1.

5. Introduction of Val Group Into Fmoc-His(Trt)-Leu-Thr-Cys(StBu)-Resin

Fmoc-Val-His(Trt)-Leu-Thr-Cys(StBu)-Resin was prepared in a manner as described in Example 1.

6. Removal of Peptide Chain From Resin

Val-His-Leu-Thr-Cys was prepared in a manner as described in Example 1.

7. Introduction of Fructose Into Peptide Chain Due to Amadori Rearrangement Reaction Fructose-Val-His-Leu-Thr-Cys was prepared in a manner as described in Example 1.

(Preparation of Peptide Fructose-Protein Conjugate)

In this example, CGG, BSA and KLH were used as proteins.

1. Preparation of CGG-Cys-Thr-Leu-His-Val-Fructose 200 mg ($1.33 \times 10^{-3}$ mmol) of CGG was dissolved in about 10 ml of PBS. To this mixture, a solution, in which 20.9 mg (0.0667 mmol, 50 eq.) of SPDP was dissolved in 1 ml of ethanol, was gradually added at room temperature while stirring. After stirring for 30 minutes, the mixture was subjected to purification using a Sephadex G25M column to obtain 24 ml (2.07 mg/ml) of CGG-SPDP solution. The number of SPDPs introduced into CGG was measured in the following manner.

0.5 ml of CGG-SPDP solution was collected, and the absorbance at 280 nm (A280) was measured, with a result of 6.03. Thereafter, 25 µl of 100 mM dithiothreitol solution was added to the CGG-SPDP solution, and the mixture was allowed to stand for 3 minutes. Thereafter, the absorbance at 343 nm (A343) was measured, with a result of 4.67. The 343-nm absorbance was attributed to pyridine-2-thione released due to DTT reduction. The amount of pyridine-2-thione is equivalent to the amount of the introduced SPDP. Therefore, the SPDP concentration [SPDP] can be calculated by formula (8) below, where the molar absorbance coefficient of pyridine-2-thione at 343 nm is 8080.

$$[SPDP] = 4.67/8080 \qquad \text{(Formula 8)}$$
$$= 5.780 \times 10^{-4} \text{ (M)}$$

280-nm absorption is attributed to the protein. The introduced SPDP absorbs 280-nm light. Therefore, calculation of the CGG concentration [CGG] requires correction represented by formula (9) below, where the molar absorbance coefficient of SPDP at 280 nm is 5100, the molar absorbance coefficient of CGG at 280 nm is $1.99 \times 10^5$, (A280, SPDP) represents absorbance at 280 nm attributed to SPDP, and (A280, CGG) represents absorbance at 280 nm attributed to CGG.

$$(A280, SPDP) = 5.780 \times 10^{-4} \times 5100 \qquad \text{(Formula 9)}$$
$$= 2.95$$
$$(A280, CGG) = 6.03 - 2.95$$
$$= 3.08$$
$$[CGG] = 3.08/(1.99 \times 10^5)$$
$$= 1.55 \times 10^{-5} \text{ (M)}$$

Therefore, the number of SPDP molecules introduced into one CGG molecule [SPDP]/[CGG] is indicated by formula (10) below.

$$[SPDP]/[CGG] = 37.3 \qquad \text{(Formula 10)}$$

Into a PBS solution of the resultant CGG-SPDP (2.32 mg/ml, 13.5 ml), 11.7 mg (0.016 mmol, 2 eq. SPDP) of fructose-Val-His-Leu-Thr-Cys dissolved in 0.1 ml of PBS was dropped at room temperature while stirring. The mixture was mildly stirred at room temperature for 3 hours. The reaction was tracked by measuring the absorbance of the reaction solution at 343 nm. The reaction solution was subjected to purification using a Sephadex G25M column to obtain 32 ml (0.885 mg/ml) of CGG-Cys-Thr-Leu-His-Val-fructose. Hereinafter, this peptide fructose-protein conjugate is abbreviated as F-CGG.

2. Preparation of KLH-Cys-Thr-Leu-His-Val-Fructose 57.8 mg ($5.78 \times 10^{-4}$ mmol) of KLH was dissolved in about 10 ml of PBS. To this mixture, a solution, in which 2.7 mg (0.00867 mmol, 15 eq.) of SPDP was dissolved in 1 ml of ethanol, was gradually added at room temperature while stirring. After stirring for 30 minutes, the mixture was subjected to purification using a Sephadex G25M column to obtain 28 ml (1.47 mg/ml) of KLH-SPDP solution. The number of SPDPs introduced into KLH was measured in the following manner.

0.5 ml of KLH-SPDP solution was collected, and the absorbance at 280 nm (A280) was measured, with a result of 1.88. Thereafter, 25 µl of 100 mM dithiothreitol solution was added to the CGG-SPDP solution, and the mixture was allowed to stand for 3 minutes. Thereafter, the absorbance at 343 nm (A343) was measured, with a result of 0.365. The 343-nm absorbance was attributed to pyridine-2-thione released due to DTT reduction. The amount of pyridine-2-thione is equivalent to the amount of the introduced SPDP. Therefore, the SPDP concentration [SPDP] can be calculated by formula (11) below, where the molar absorbance coefficient of pyridine-2-thione at 343 nm is 8080.

$$\{SPDP\} = 0.365/8080 \qquad \text{(Formula 11)}$$
$$= 4.517 \times 10^{-5} \text{ (M)}$$

280-nm absorption is attributed to the protein. The introduced SPDP absorbs 280-nm light. Therefore, calculation of the KLH concentration [KLH] requires correction represented by formula (12) below, where the molar absorbance coefficient of SPDP at 280 nm is 5100, the molar absorbance coefficient of KLH at 280 nm is $1.12 \times 10^5$, and (A280, KLH) represents absorbance at 280 nm attributed to KLH.

$$(A280, \text{SPDP}) = 4.517 \times 10^{-5} \times 5100 \quad \text{(Formula 12)}$$
$$= 0.230$$
$$(A280, \text{KLH}) = 1.88 - 0.230$$
$$= 1.65$$
$$[\text{KLH}] = 1.65/(1.12 \times 10^5)$$
$$= 1.47 \times 10^{-5} (M)$$

Therefore, the number of SPDP molecules introduced into one KLH molecule [SPDP]/[KLH] is indicated by formula (13) below.

$$[SPDP]/[KLH] = 3.07 \quad \text{(Formula 13)}$$

Into a PBS solution of the resultant KLH-SPDP (2.65 mg/ml, 15.5 ml), 8.81 mg (0.012 mmol, 10 eq. SPDP) of fructose-Val-His-Leu-Thr-Cys dissolved in 0.1 ml of PBS was dropped at room temperature while stirring. The mixture was mildly stirred at room temperature for 3 hours. The reaction was tracked by measuring the absorbance of the reaction solution at 343 nm. The reaction solution was subjected to purification using a Sephadex G25M column to obtain 32 ml (1.13 mg/ml) of KLH-Cys-Thr-Leu-His-Val-fructose. Hereinafter, this peptide fructose-protein conjugate is abbreviated as F-KLH.

3. Preparation of BSA-Cys-Thr-Leu-His-Val-Fructose 200 mg (0.00303 mmol) of BSA was dissolved in about 10 ml of PBS. To the mixture, a solution, in which 4.73 mg (0.0152 mmol, 5 eq.) of SPDP was dissolved in 1 ml of ethanol, was gradually added at room temperature while stirring. After stirring for 30 minutes, the mixture was subjected to purification using a Sephadex G25M column to obtain 16 ml (10.4 mg/ml) of BSA-SPDP solution. The number of SPDPs introduced into BSA was measured in the following manner.

0.5 ml of BSA-SPDP solution was collected, and the absorbance at 280 nm (A280) was measured, with a result of 9.18. Thereafter, 25 µl of 100 mM dithiothreitol solution was added to the BSA-SPDP solution, and the mixture was allowed to stand for 3 minutes. Thereafter, the absorbance at 343 nm (A343) was measured, with a result of 3.63. The 343-nm absorbance was attributed to pyridine-2-thione released due to DTT reduction. The amount of pyridine-2-thione is equivalent to the amount of the introduced SPDP. Therefore, the SPDP concentration [SPDP] can be calculated by formula (14) below, where the molar absorbance coefficient of pyridine-2-thione at 343 nm is 8080.

$$[\text{SPDP}] = 3.63/8080 \quad \text{(Formula 14)}$$
$$= 4.493 \times 10^{-4} (M)$$

280-nm absorption is attributed to the protein. The introduced SPDP absorbs 280-nm light. Therefore, calculation of the BSA concentration [BSA] requires correction represented by formula (15) below, where the molar absorbance coefficient of SPDP at 280 nm is 5100, the molar absorbance coefficient of BSA at 280 nm is $4.36 \times 10^4$, and (A280, BSA) represents absorbance at 280 nm attributed to BSA.

$$(A280, \text{SPDP}) = 4.493 \times 10^{-4} \times 5100 \quad \text{(Formula 15)}$$
$$= 2.29$$
$$(A280, \text{BSA}) = 9.18 - 2.29$$
$$= 6.89$$
$$[\text{BSA}] = 6.89/(4.36 \times 10^4)$$
$$= 1.58 \times 10^{-4} (M)$$

Therefore, the number of SPDP molecules introduced into one BSA molecule [SPDP]/[BSA] is indicated by formula (16) below.

$$[SPDP]/[BSA] = 2.8 \quad \text{(Formula 16)}$$

Into a PBS solution of the resultant BSA-SPDP (10.4 mg/ml, 16 ml), 10.3 mg (0.014 mmol, 2 eq. SPDP) of fructose-Val-His-Leu-Thr-Cys dissolved in 0.1 ml of PBS was dropped at room temperature while stirring. The mixture was mildly stirred at room temperature for 3 hours. The reaction was tracked by measuring the absorbance of the reaction solution at 343 nm. The reaction solution was subjected to purification using a Sephadex G25M column to obtain 24 ml (6.51 mg/ml) of BSA-Cys-Thr-Leu-His-Val-fructose. Hereinafter, this peptide fructose-protein conjugate is abbreviated as F-BSA.

(Preparation of Antiserum and Evaluation of its Performance)

Among the prepared peptide fructose-protein conjugates, F-CGG and F-KLH were used as immunogens to prepare an antiserum by the method below. Combinations of immunogens and animals to be immunized used in preparing antisera are shown in Table 2.

TABLE 2

Immunization Method

| Immunogen | Animal | Sex | Number of animals | Age (weeks) (at first immunization) |
|---|---|---|---|---|
| F-CGG | Mouse (BALB/C) | ♀ | 5 | 7 |
| F-KLH | Mouse (A/J) | ♀ | 5 | 7 |

Figure 1:
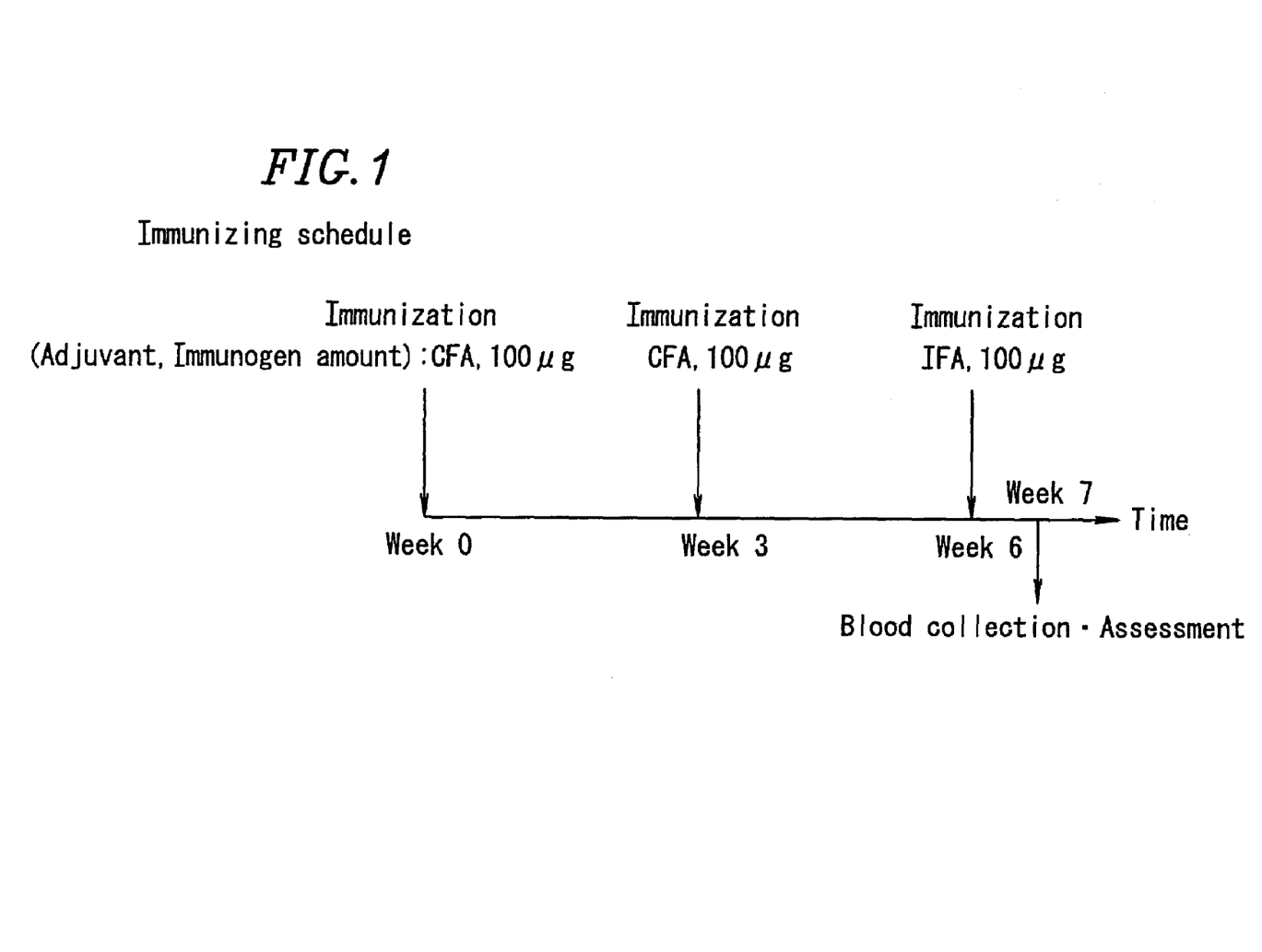
FIG. 1 shows an immunizing schedule used in one embodiment of the present invention.
Figure 2:
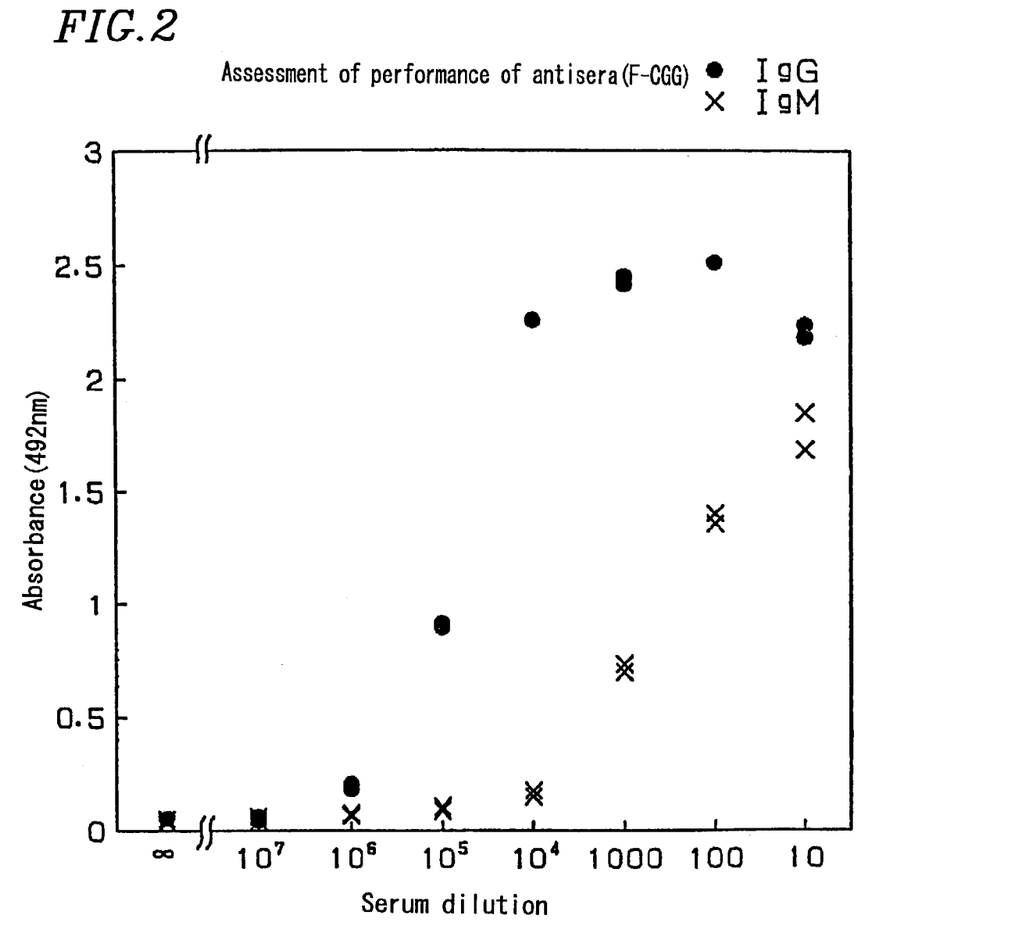
FIG. 2 is a diagram showing the performance assessment of an antiserum for one embodiment (F-CGG) of the present invention.
Figure 3:
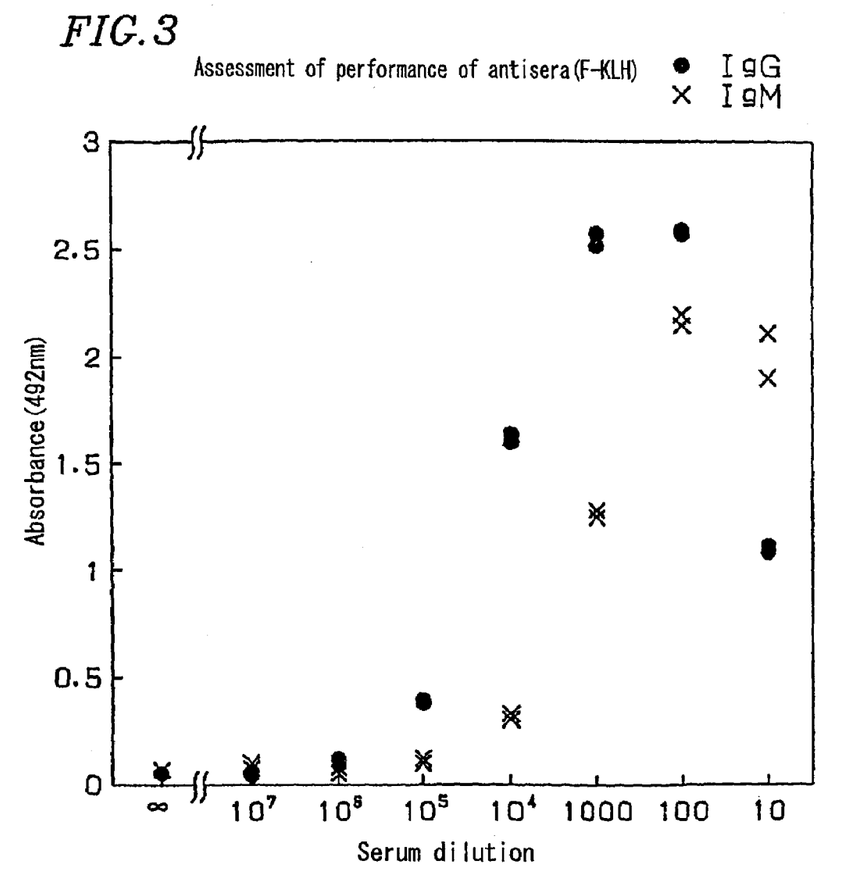
FIG. 3 is a diagram showing the performance assessment of an antiserum for one embodiment (F-KLH) of the present invention.

In immunization, F-CGG or F-KLH was mixed with complete Freund's adjuvant (CFA) or incomplete Freund's adjuvant (IFA) using a homogenizer. The mixture was injected into animals to be immunized. The final protein concentration of the mixture was 1 mg/ml. The two immunogens were used to perform immunization in accordance with the immunizing schedule shown in FIG. 1. Antisera collected 7 weeks after first immunization were assessed for their performance using ELISA. Conditions for ELISA are shown in Table 3. The results of assessment when the immunogen was F-CGG are shown in FIG. 2. The results of assessment when the immunogen was F-KLH are shown in FIG. 3. In FIGS. 2 and 3, the horizontal axis represents the dilution of the serum, and the vertical axis represents absorbance at a measurement wavelength of 492 nm. Note that in FIGS. 2 and 3, a measurement point at the infinity of the serum dilution shows the measurement result of a sample which did not contain serum.

TABLE 3

Conditions for ELISA

| | |
|---|---|
| Antigen coating: | F-BSA, 0.1 mg/ml, 100 μl/well, r.t., overnight |
| Blocking: | 1% BSA.PBS.Az, 200 μl/well, r.t., 30 minutes |
| Primary antibody: | a dilution series of each antiserum (1% BSA.PBS.Az), r.t., 3 hours |
| Secondary antibody: | anti-mouse IgG-POD or anti-mouse IgM-POD, 0.2 μg/ml 1% BSA.PBS, r.t., 30 minutes |
| Enzymatic reaction: | o-phenylenediamine, 4 mg/ml PCB + 30% $H_2O_2$, r.t., 3 minutes |
| Termination of reaction: | $4NH_2SO_4$, 25 μl/well |

The titers of the antiserum obtained from F-CGG as an immunogen and the antiserum obtained from F-KLH as an immunogen were both observed at a serum dilution of $10^5$ to $10^6$. Since the amount of produced IgG was larger than that of produced IgM, F-CGG and F-KLH have good performance.

Example 3

Preparation of Monoclonal Antibody

In this example, CGG and KLH were used as proteins for preparing conjugates employed as immunogens. As a myeloma-derived cell, p3×63·Ag8·653 was used. ELISA was adopted as an assessment method for cell screening. A conjugate containing BSA as a protein was prepared and used as a control for ELISA.

(Preparation of Conjugate to Be Used as Immunogen)

1. Preparation of pyridyldithiopropionylated CGG (Preparation of CGG-SPDP)

200 mg ($1.33 \times 10^{-3}$ mmol) of CGG was dissolved in 50 ml of phosphate buffer saline (hereinafter abbreviated as PBS). 5 ml of SPDP/ethanol solution (SPDP=40 mg, 0.13 mmol, an equivalent weight of 100) was dropped into the mixture while stirring. After stirring at room temperature for 30 minutes, the resultant precipitate was removed by centrifugation (10 minutes, 20,000 rpm). The resultant supernatant was subjected to gel filtration using a Sephadex G25M column (manufactured by Pharmacia, diameter 2 cm×length 80 cm) to obtain 80 ml of CGG-SPDP/PBS solution.

The number of SPDPs binding to one CGG molecule was determined as follows. 1 ml of the resultant CGG-SPDP PBS solution was used and the absorbance thereof was measured at 280 nm. The absorbance was 3.73.

50 μl of 100 mM dithiothreitol (hereinafter abbreviated as DTT) aqueous solution was added to the CGG-SPDP/PBS solution, and was allowed to stand for 5 minutes. Thereafter, the absorbance was measured at 343 nm, with a result of 2.80.

Assuming that the molecular absorbance coefficient of pyridine-2-thione released by DTT reduction at 343 nm was $8.08 \times 10^3$, the concentration [pyridine-2-thione] was determined by formula (A).

$$[\text{pyridine-2-thione}] = 2.80/(8.08 \times 10^3) \quad \text{(Formula A)}$$
$$= 3.47 \times 10^{-4} (M)$$

This concentration is equivalent to the concentration of SPDP introduced into CGG. Also, since the 2-pyridyldisulfide group of SPDP contributes to the absorbance at 280 nm, calculation of the CGG concentration requires the following correction. The absorbance at 280 nm attributed to CGG ($A_{280, CGG}$) can be calculated by formula (B) below, where the molecular absorbance coefficient of a 2-pyridyldisulfide group at 280 nm is $5.1 \times 10^3$.

$$A_{280,CGG} = 3.73 - (3.47 \times 10^{-4} \times 5.1 \times 10^3) \quad \text{(Formula B)}$$
$$= 1.96$$

Therefore, the CGG concentration [CGG], and the number of SPDP molecules introduced into one CGG molecule [SPDP]/[CGG] can be calculated by formula (C) below, where the molar absorbance coefficient of CGG at 280 nm is $1.99 \times 10^5$.

$$[CGG] = 1.96/(1.99 \times 10^5) \quad \text{(Formula C)}$$
$$= 9.85 \times 10^{-6} (M)$$
$$[SPDP]/[CGG] = 3.47 \times 10^{-4}/(9.85 \times 10^{-6})$$
$$= 35.2$$

2. Preparation of Conjugate of Peptide Fructose and CGG 40 mg ($7.18 \times 10^{-2}$ mmol) of a pyridyldithio-derivative was added to 50 ml of CGG-SPDP/PBS solution, and stirred at 4° C. overnight. The resultant precipitate was removed by centrifugation (10 minutes, 20,000 rpm), and thereafter, the absorbance ($A_{343}$) was measured at 343 nm, with a resulting of $A_{343}$=3.52. The resultant supernatant was subjected to gel filtration using a Sephadex G25 column (manufactured by Pharmacia, diameter 2 cm×length 80 cm). As a result, 48 ml of a conjugate of peptide fructose and CGG was obtained.

The number of peptide fructoses binding to one CGG molecule was determined as follows. Assuming that the molecular absorbance coefficient of released pyridine-2-thione at 343 nm is $8.08 \times 10^3$ based on the above-described result that $A_{343}$ was 3.52 immediately after the reaction, the concentration [pyridine-2-thione] can be calculated by formula (D) below.

$$[\text{pyridine-2-thione}] = 3.52/(8.08 \times 10^3) \quad \text{(Formula D)}$$
$$= 4.35 \times 10^{-4} (M)$$

This concentration is equivalent to the concentration of peptide fructose introduced into CGG. Since the CGG concentration was $1.40 \times 10^{-5}$ M, the number of peptide fructose molecules introduced into one CGG molecule [peptide fructose]/[CGG] can be calculated by formula (E).

$$[\text{peptide fructose}]/[CGG] = 4.35 \times 10^{-4}/1.40 \times 10^{-5} \quad \text{(Formula E)}$$
$$= 31.1$$

3. Preparation of Conjugate of KLH and Peptide Fructose 54 mg of KLH and 5.42 mg (30 eq.) of SPDP were used to prepare pyridyldithiopropionylated KLH (KLH-SPDP) in a manner as described above concerning CGG, with a result of 28 ml of KLH-SPDP/PBS solution (concentration: 1.47 mg/ml). The number of SPDPs introduced into one KLH molecule was 3.0.

15.5 ml (41.1 mg) of the resultant KLH-SPDP solution was used to react with peptide fructose (6.4 mg) as described above, with a result of 33.3 mg (3.33 mg/ml, 10 ml) of a conjugate of KLH and peptide fructose. The number of peptide fructoses introduced into one KLH molecule was 2.7.

4. Preparation of Conjugate of BSA and Peptide Fructose

A conjugate of peptide fructose and BSA was prepared as a control for ELISA. 200 mg of BSA and 4.73 mg (5 eq.) of SPDP were used to prepare pyridyldithiopropionylated BSA (BSA-SPDP) in a manner as described above concerning CGG and KLH, with a result of 16 ml of BSA-SPDP/PBS solution (concentration: 10.4 mg/ml). The number of SPDPs introduced into one BSA molecule was 2.8.

16 ml of the resultant BSA-SPDP solution was used to react with peptide fructose (7.4 mg) in a manner as described above, with a result of 156.2 mg (6.51 mg/ml, 24 ml) of a conjugate of peptide fructose and BSA. The number of peptide fructoses introduced into one BSA molecule was 2.5.

(Method of Preparing Monoclonal Antibody-Producing Cells and Monoclonal Antibody)

1. Immunization of Mice

Ten about 8-week old mice (Balb/c) were divided into two groups (five for each). Two immunogens (CGG conjugate and KLH conjugate) as prepared above were intraperitoneally injected into the respective groups at a dose of 100 µL.

2. Check of Antibody Production 50 to 100 µL of blood was collected into a centrifuge tube from the ophthalmic vein of mice, which were bled 77 days after injection for immunization. The sera were centrifuged, followed by assessment of antibody titer using ELISA (described below). As a result, production of anti-HbA1c antibodies was confirmed in all of the mice.

3. Booster for Mice

Booster injection of a weak immunogen was performed for mice having a particularly high titer in the above-described antibody titer assessment in order to enlarge the spleens of the mice (the group of mice given the CGG conjugates as an immunogen). The immunogen was 1 mg/mL solution, in which the CGG conjugate with fructose was diluted in PBS, without any adjuvant.

4. Cell Fusion

Three days after the booster, spleen cells were isolated from the mice. The spleen cells were fused with a mouse myeloma-derived cell line (P3×63–Ag8.653) by a commonly used method using polyethylene glycol having an average molecular weight of 1,500. Spleen cells from the same mice were used as feeder cells (cells supplying a growth factor). The fused cells were cultured in HAT medium containing 15% fetal calf serum (hereinafter abbreviated as FCS) on two 96-well plates. After one week, the medium was exchanged with HT medium containing 15% FCS.

5. Cloning

Antibody titers were measured using ELISA. The 5 wells having the highest titers were selected.

The media in the 5 wells were diluted and dispensed on five 96-well plates at a density of one cell per well (limiting dilution). Thymus cells from 5 week old mice (Balb/c) were used as feeder cells to promote initial growth. The cells were further cultured while increasing the size of the plate. The supernatant was subjected to ELISA so as to measure antibody titers at appropriate times. A group of cells, which exhibited a high titer to HbA1c and good growth, were finally selected, and were cultured to a concentration of $5 \times 10^5$ cells/mL in 200 ml.

6. The supernatant of the finally selected cells was centrifuged. The cells were suspended in 1 ml of solution containing FCS and dimethylsulfoxide (9:1) at a concentration of $5 \times 10^6$ cells/mL. The suspension was frozen at −80° C. and was transferred to liquid nitrogen for long-term preservation.

7. A monoclonal antibody was purified from the supernatant of the culture medium by affinity chromatography using 2-mercaptopyridine-binding gel (HiTrap IgM Purification, manufactured by Pharmacia). The monoclonal antibody was confirmed to be IgM according to the test using a Mouse Monoclonal Typing Kit (manufactured by Binding Site).

(Measurement of Antibody Titer by ELISA)

The antisera and culture supernatants obtained in the preparation of the above-described antibody were assessed by ELISA. Conditions and methods for the measurement are described below.

1. Antigen Coating

A conjugate of peptide fructose and BSA was diluted with PBS containing 0.1 mg/ml and 0.04% sodium azide (BSA•PBS•Az) to prepare an antigen solution having a BSA concentration of 0.1 mg/mL. 100 µL of the antigen solution was plated per well in microplates (vinyl chloride 96-well plates manufactured by Costar), and allowed to stand at 20° C. overnight. An aspirator was used to remove the antigen solution, and thereafter, the microplates were washed with PBS three times. The remaining PBS was removed by an aspirator.

Purified HbA1c and purified HbA0 were optionally used as antigens for coating depending on the measurement. In this case, the antigen concentration was 0.02 mg/ml, and after plating into wells, the antigen solution was allowed to stand at 4° C. overnight.

2. Blocking

200 µL of 1% BSA•PBS•Az was plated per well, and allowed to stand for 30 minutes at room temperature. Thereafter, BSA•PBS•Az was removed using an aspirator, and the plates were washed with PBS three times. If subsequent procedures were not performed on the same day, the plates remaining in this state were preserved at 4° C. along with a filter wetted with water.

3. Reaction of Antibody

100 µL of antibody solution (a serum, a culture supernatant, a purified antibody, or the like), diluted to various dilutions with 1% BSA•PBS•Az, was plated per well of the plates prepared with the above-described procedures. The plates were allowed to stand at room temperature for 3 hours. Thereafter, the antibody solution was removed using an aspirator. The plates were washed with PBS three times. The remaining PBS was removed using an aspirator.

4. Reaction of Secondary Antibody 0.2 µg/mL peroxidase-labeled goat anti-mouse IgG or IgM antibody (manufactured by KPL) was dissolved in 1% BSA/PBS solution (secondary antibody solution). 100 µL of the secondary antibody solution was plated per well of plates and allowed to stand at room temperature for 30 minutes. An aspirator was used to remove the secondary antibody solution. The plates were washed with PBS three times. The remaining PBS was removed using an aspirator.

5. Reaction of Substrate and its Termination 40 mg of o-phenylenediamine (for biochemistry) was dissolved in 10 mL of citrate-phosphate buffer (pH 5). 4 μL of 30% hydrogen peroxide was added to the mixture immediately before use (substrate solution). 100 μL of the substrate solution was plated per well and allowed to stand at room temperature. After 3 to 5 minutes, 25 μl of 4N sulfuric acid was added per well to terminate the reaction.

6. Measurement

Absorbance was measured at 492 nm using a microplate reader (manufacture by Tosoh Corporation).

(Results of Measurement of Antibody Titers)

Figure 4:
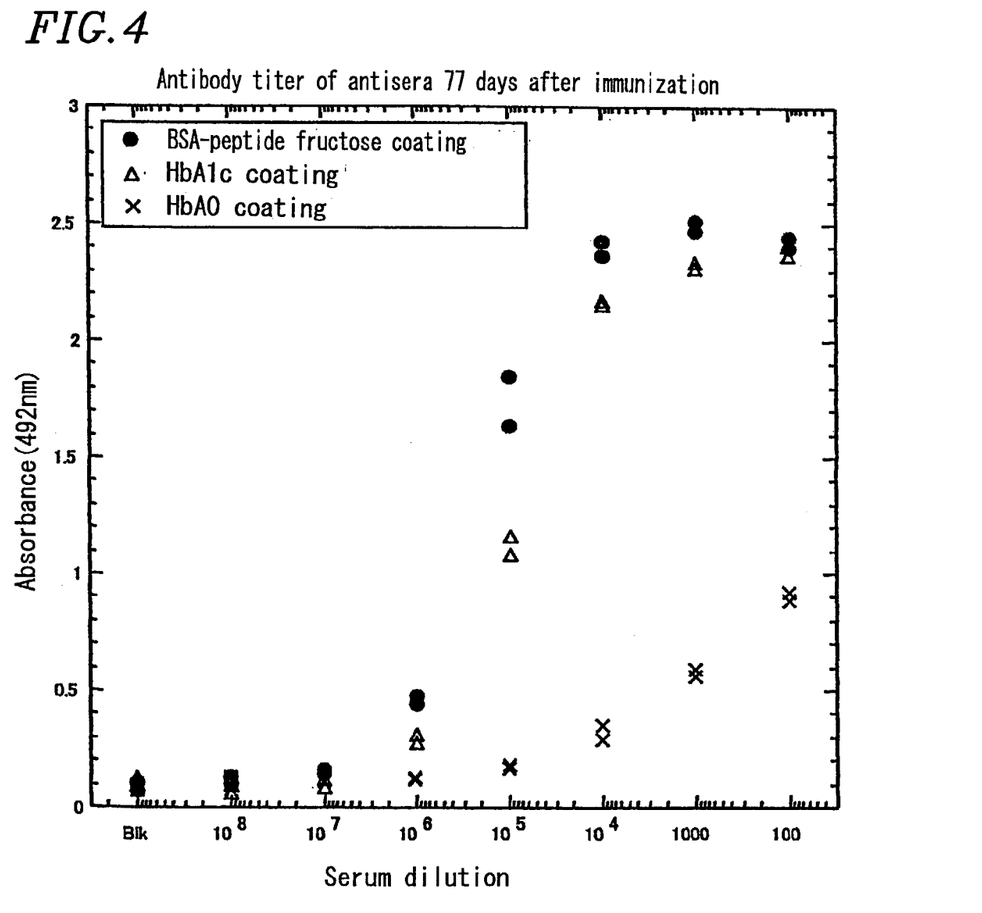
FIG. 4 is a diagram showing the antibody titer of an antiserum 77 days after immunization according to one embodiment of the present invention.
Figure 5:
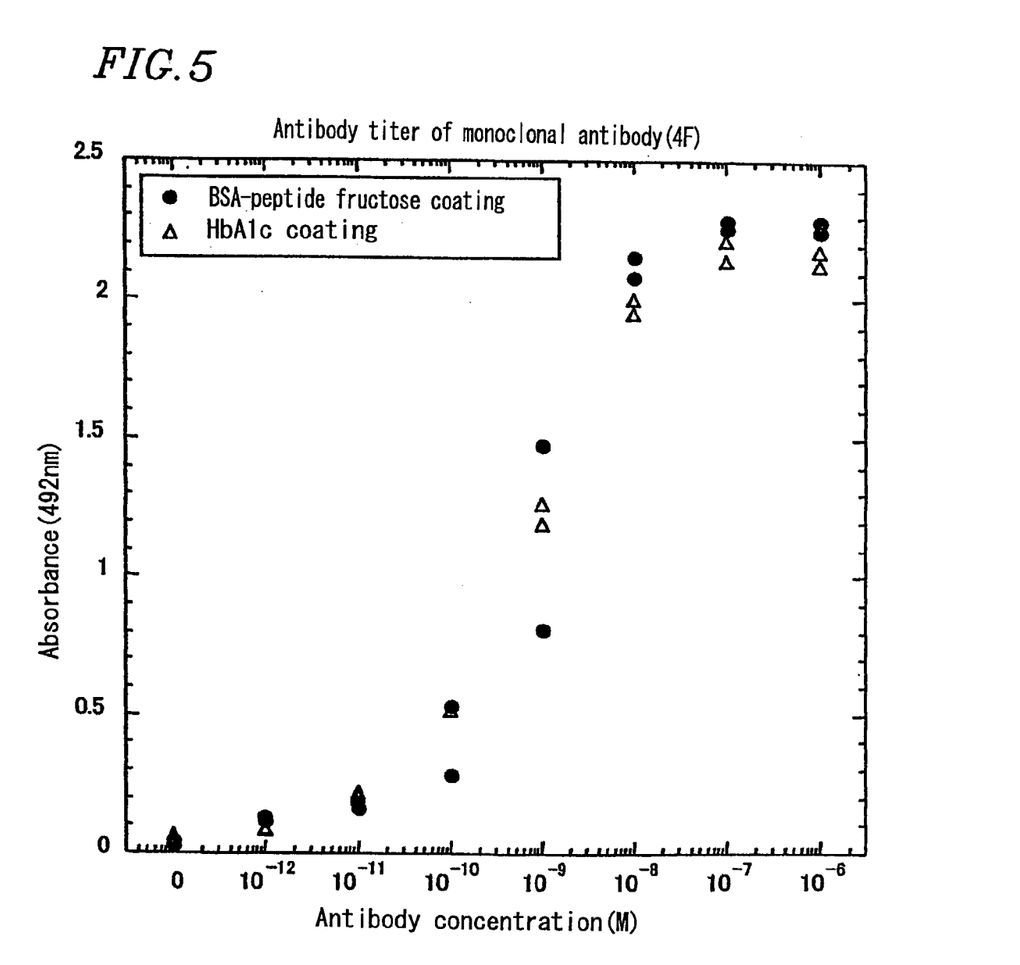
FIG. 5 is a diagram showing the antibody titer of a monoclonal antibody (4F) according to one embodiment of the present invention.
Figure 6:
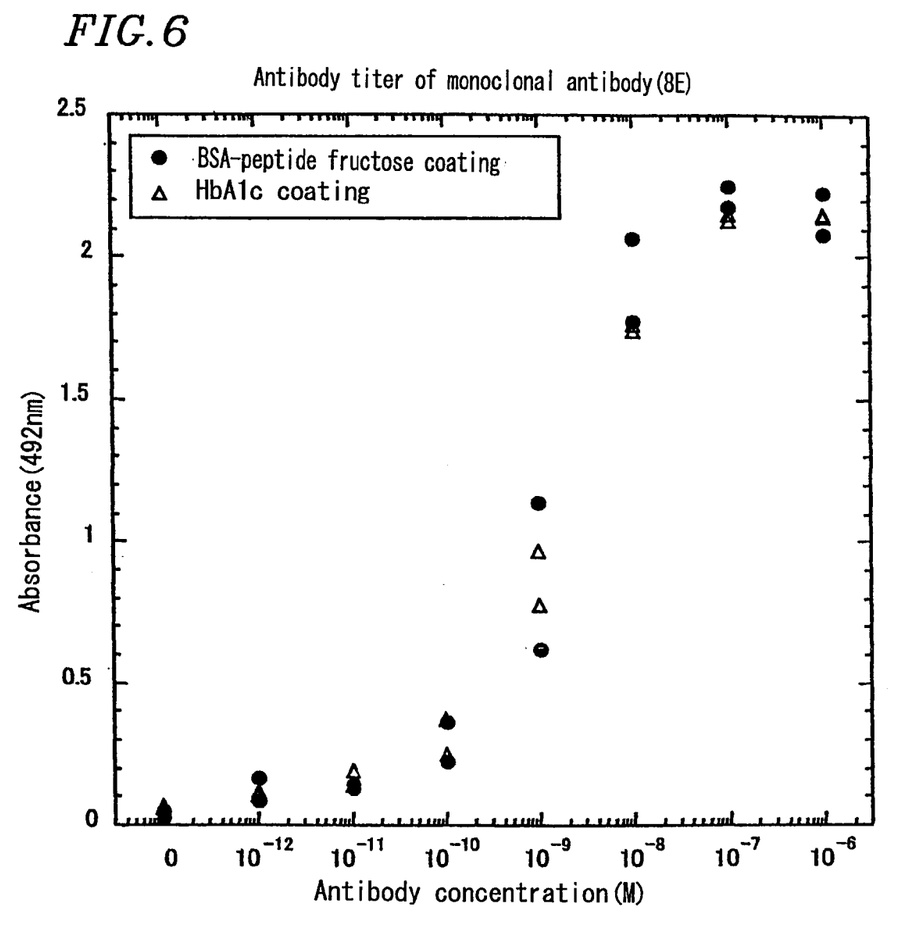
FIG. 6 is a diagram showing the antibody titer of a monoclonal antibody (8E) according to one embodiment of the present invention.

The results of measurement of the antibody titer of an antiserum collected immediately before cell fusion (77 days after immunization) according to the above-described methods are shown in FIG. 4. The results of measurement of the antibody titers of monoclonal antibodies obtained by purifying the culture supernatants of two clones (4F and 8E) selected by cloning are shown in FIG. 5 (4F) and FIG. 6 (8E).

The result of FIG. 4 shows that 77 days after immunization, the antiserum had capability of binding similarly to BSA-peptide fructose and HbA1c, and substantially no capability of binding to HbA0. Therefore, it is believed that this antiserum recognizes the fructose binding site of HbA1c as originally aimed.

Further, it is indicated that the two clones selected by cloning after cell fusion (4F and 8E) have a binding ability of $1 \times 10^{-9}$ M and $3 \times 10^{-9}$ M, respectively at the half value of the binding ability.

Deposit

Two hybridomas obtained in the present invention were deposited with the International Patent Organism Depository, the National Institute of Advanced Industrial Science and Technology (address: AIST Tsukuba Central 6, 1-1, Higashi, 1-Chome Tsukuba-shi, Ibaraki-ken, 305-8566 Japan) on Jun. 22, 2001 under designation FERM BP-7637 and FERM BP-7636.

INDUSTRIAL APPLICABILITY

As described above, an —SH group is introduced into the peptide fructose of the present invention in addition to fructose-valine-histidine which is a characteristic structure of HbA1c. Therefore, it is easy for the peptide fructose to be linked to a protein. By linking the peptide fructose to a protein, a protein conjugate can be produced.

The peptide fructose-protein conjugate of the present invention has fructose-valine-histidine which is a characteristic structure of HbA1c and a protein other than hemoglobin. Therefore, this protein conjugate has no structure common to hemoglobins other than HbA1c. Therefore, by using this protein conjugate as an immunogen, anti-HbA1c antibodies which do not have cross reactivity to HbA0, and preferably do not have cross reactivity to hemoglobin other than HbA1c, can be reliably produced.

The present invention relates to a monoclonal antibody-producing cell obtained by fusing a mouse spleen cell, which has been sensitized with a conjugate of peptide fructose including a formula (I) and a protein, with a myeloma-derived cell line, followed by cloning, and a monoclonal antibody produced by the monoclonal antibody-producing cell. Therefore, it is possible to provide a monoclonal antibody specific to HbA1c in human hemoglobin, and an antibody-producing cell producing the monoclonal antibody.

The invention claimed is:

1. A protein conjugate, comprising a peptide fructose linked with a protein, and the peptide fructose compound is represented by formula (I) below:

wherein R1 represents a cysteine residue, the R1 is linked to the carboxy-terminus of R2 at (b) with a covalent bond, the R2 contains two or more amino acids derived from the amino acid sequence of HbA1 or an amino acid analog functionally equivalent to the amino acids, and the R2 is linked to the fructose at the amino-terminus thereof, and the protein is CGG, wherein the peptide fructose compound is linked to CGG at R1.

2. A protein conjugate according to claim 1, wherein the R2 contains at least a peptide represented by formula (II) below:

3. A protein conjugate according to claim 1, wherein the R2 contains at least a peptide represented by formula (III) below:

4. A protein conjugate according to claim 1, wherein the covalent bond at (b) is a peptide bond.

5. An antiserum, produced in the blood of an animal by injecting a protein conjugate according to claim 1 into said animal.

6. An antibody, isolated from an antiserum according to claim 5.

7. An isolated monoclonal antibody-producing cell, wherein the monoclonal antibody-producing cell is obtained by fusing a spleen cell of a mouse sensitized with a protein conjugate according to claim 1, with a myeloma-derived cell, and cloning a fused cell, and the monoclonal antibody-producing cell produces a monoclonal antibody capable of specifically binding to human hemoglobin A1c.

8. The monoclonal antibody-producing cell according to claim 7, designated as deposit number FERM BP-7637 or FERM BP-7636.

9. A method of producing a monoclonal antibody-producing cell capable of producing a monoclonal antibody capable of specifically binding to human hemoglobin A1c, the method comprising the steps of:
   a) sensitizing a mouse with a protein conjugate according to claim 1; and
   b) isolating a spleen cell from the sensitized mouse, and fusing the spleen cell with a myeloma-derived cell.

10. A monoclonal antibody, produced by a monoclonal antibody-producing cell according to claim 7, which specifically binds to human hemoglobin A1c.

11. A monoclonal antibody produced by the monoclonal antibody-producing cell sensitized with a protein conjugate according to claim 1, wherein the binding constant to human hemoglobin A1c thereof is $10^4$ or more.

* * * * *